(12) United States Patent
Taylor

(10) Patent No.: US 10,009,667 B2
(45) Date of Patent: Jun. 26, 2018

(54) SYSTEM AND METHOD FOR MONITORING GAS EMISSION OF PERISHABLE PRODUCTS

(71) Applicant: Wal-Mart Stores, Inc., Bentonville, AR (US)

(72) Inventor: Joseph D. Taylor, Pullman, WA (US)

(73) Assignee: Walmart Apollo, LLC, Bentonville, AR (US)

( * ) Notice: Subject to any disclaimer, the term of this patent is extended or adjusted under 35 U.S.C. 154(b) by 0 days. days.

(21) Appl. No.: 15/541,160

(22) PCT Filed: Dec. 29, 2015

(86) PCT No.: PCT/US2015/067902
§ 371 (c)(1),
(2) Date: Jun. 30, 2017

(87) PCT Pub. No.: WO2016/109563
PCT Pub. Date: Jul. 7, 2016

(65) Prior Publication Data
US 2018/0007453 A1  Jan. 4, 2018

Related U.S. Application Data

(60) Provisional application No. 62/098,948, filed on Dec. 31, 2014.

(51) Int. Cl.
*G08B 21/00* (2006.01)
*H04Q 9/00* (2006.01)
*G01N 33/02* (2006.01)

(52) U.S. Cl.
CPC .............. *H04Q 9/00* (2013.01); *G01N 33/02* (2013.01); *H04Q 2209/30* (2013.01); *H04Q 2209/40* (2013.01); *H04Q 2209/823* (2013.01)

(58) Field of Classification Search
USPC ...................................... 340/870.16
See application file for complete search history.

(56) References Cited

U.S. PATENT DOCUMENTS 5,621,162 A    4/1997  Yun
6,435,002 B1   8/2002  Briggs
(Continued)

FOREIGN PATENT DOCUMENTS

CN    202306566 U    7/2012
CN    103543703 A    1/2014
(Continued)

OTHER PUBLICATIONS

Eom, Ki-Hwan, et al.; "The Meat Freshness Monitoring System Using the Smart RFID Tag", International Journal of Distributed Sensor Networks, vol. 2014, Jul. 9, 2014, http://journals.sagepub.com/doi/10.1155/2014/591812, pp. 1-10.
(Continued)

*Primary Examiner* — Santiago Garcia
(74) *Attorney, Agent, or Firm* — Fitch, Even, Tabin & Flannery LLP

(57) ABSTRACT

A system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

14 Claims, 4 Drawing Sheets

(56) References Cited

U.S. PATENT DOCUMENTS

| | | |
|---|---|---|
| 6,982,640 B2 | 1/2006 | Lindsay |
| 7,148,803 B2 | 12/2006 | Bandy |
| 7,271,720 B2 | 9/2007 | Tabe |
| 7,560,013 B2 | 7/2009 | Shekarriz |
| 7,954,712 B2 | 6/2011 | Babcock |
| 2004/0018641 A1* | 1/2004 | Goldsmith ............... C12Q 1/22 436/518 |
| 2004/0069046 A1 | 4/2004 | Sunshine |
| 2004/0204881 A1 | 10/2004 | Mayer |
| 2005/0197912 A1 | 9/2005 | Wittmer |
| 2005/0203790 A1 | 9/2005 | Cohen |
| 2007/0076779 A1 | 4/2007 | Haarer |
| 2007/0176773 A1 | 8/2007 | Smolander |
| 2008/0073431 A1* | 3/2008 | Davis ...................... G06F 3/147 235/383 |
| 2009/0144122 A1 | 6/2009 | Ginsberg |
| 2009/0322481 A1* | 12/2009 | Marr, III ................. H04Q 9/00 340/10.1 |
| 2010/0065632 A1* | 3/2010 | Babcock ................ G06Q 10/08 235/385 |
| 2013/0176115 A1 | 7/2013 | Puleston |
| 2013/0282522 A1 | 10/2013 | Hassan |
| 2014/0313055 A1* | 10/2014 | Warkentin ............... H04Q 9/00 340/870.16 |
| 2015/0084100 A1* | 3/2015 | Sablong ............... G01N 27/126 257/253 |
| 2017/0039511 A1* | 2/2017 | Corona ................ G06K 9/6267 |

FOREIGN PATENT DOCUMENTS

| | | |
|---|---|---|
| EP | 1374688 A1 | 1/2004 |
| EP | 2165298 A1 | 3/2010 |

OTHER PUBLICATIONS

PCT; App. No. PCT/US2015/067902; International Search Report and Written Opinion dated Mar. 29, 2016.

* cited by examiner

SYSTEM AND METHOD FOR MONITORING GAS EMISSION OF PERISHABLE PRODUCTS

RELATED APPLICATION(S)

This application is filed in accordance with 35 U.S.C. 371 claiming priority to International Application No. 2015/067902, with international filing date of Dec. 29, 2015, which claims the benefit of U.S. Provisional Application No. 62/098,948, filed Dec. 31, 2014, all of which are incorporated by reference in their entirety herein.

TECHNICAL FIELD

This invention relates generally to retail sales and perishable products.

BACKGROUND

Management of fresh products is an important component of retail grocery management. With the growth of e-commerce, fresh products may become one of the main draws for shoppers to visit brick and mortar retail locations. Therefore, the success of fresh product management can heavily impact the success of the entire retail grocery operation. However, fresh products posses a special challenge in inventory management due to their perishable nature. Many factors throughout a product's supply, distribution, and retail stages can affect the freshness of the product when it arrives in the hands of a customer.

BRIEF DESCRIPTION OF THE DRAWINGS

Disclosed herein are embodiments of system, method and apparatuses for automatically monitoring merchandise in a retail sales environment. This description includes drawings, wherein.

Figure 1:
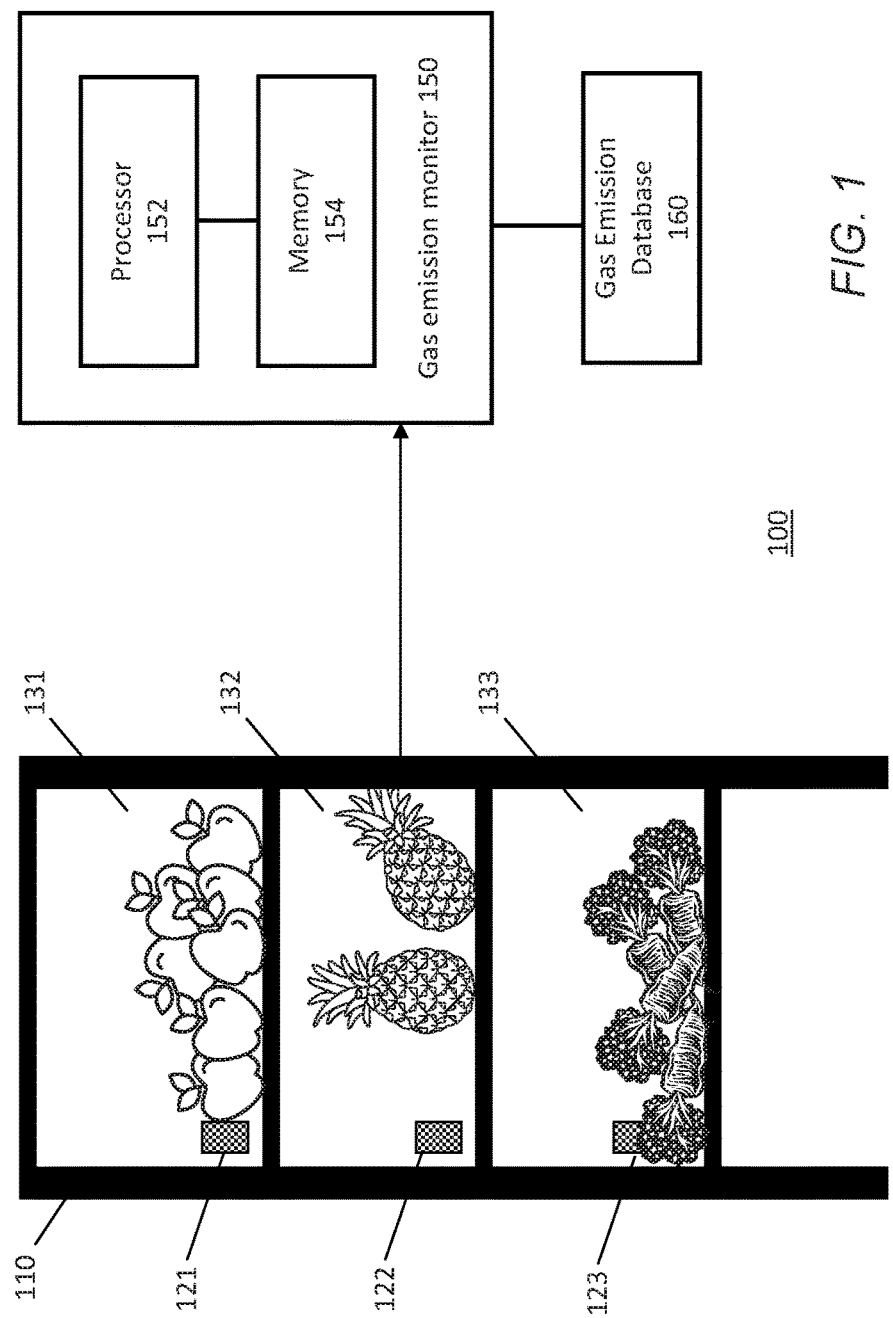
FIG. 1 is a diagram of a system in accordance with several embodiments.

Elements in the features are illustrated for simplicity and clarity and have not necessarily been drawn to scale. For example, the dimensions and/or relative positioning of some of the elements in the figures may be exaggerated relative to other elements to help improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to various embodiments, systems, apparatuses and methods are provided herein for monitoring a gas emission of products on a display fixture.

The storage and transportation of perishable goods are often rigorously tracked and logged to ensure the goods are in desired condition when they arrived at a retail location. However, conventionally, systems, technologies and processes provide minimal visibility to product freshness and placement at store level. Supply chain data provides visibility to when product is received at the store, but there is very limited visibility to where product is placed in the store (e.g. in the backroom, on the sales floor, etc.), whether or not the product has been kept within the appropriate temperature standards and the amount of lifespan remaining when the would be considered suitable for consumption. When a fresh product is kept out of appropriate temperature standards the effective lifespan before the product spoils is reduced. Variations in lifespan may also occur due to variation in product varieties and picking conditions. While this loss of product lifespan is frequently not visible on the product, it does change the gas emissions that come from the product. Improper handling of fresh product can lead customers inadvertently purchasing products that will spoil shortly after they are acquired. The inexperience of associates who work in fresh products department can also pose challenges to operational execution at store level. Smart fixtures could be used not only to evaluate the freshness level of product in store, but could also provide visibility to where products were in the store, and could provide real time data that could be used for price management (by identifying when a freshness based markdown on a collection of products was appropriate) and to create tasks for fresh area associates based on store specific fresh circumstances.

Embodiments of the disclosed system would add gas emission sensors to fixtures used to display fresh product. The sensors would measure the gas emissions from the produces displayed on the fixture. In some cases, each fixture may include a small computing device (e.g. a microprocessor or a RASPBERRY PI type device) that would be WiFi enabled.

In general terms, some embodiments provide a system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

In order to match sensor measurements of product freshness with product gas emission outputs, a database of gas emissions across product lifecycle may be used. A profile of each individual fresh product to be considered may be included or added to the system. Variations could include hand held units that measure fresh product gas emissions and or spectrometers that take measures from light producing sensors.

Referring now to FIG. 1, a system for providing a gas emission monitoring is shown. The system 100 includes a display fixture 110 having gas sensors 121, 122, and 123 in communication with a gas emission monitor 150. The display fixture 110 may be a multi-compartment shelf as shown 110 or a table, a refrigerated case, a stand, and the like. Additional examples of display fixtures are provided herein with reference to FIGS. 5-6 below. Generally, the display fixture 110 may be any fixture on the sales floor having any number of compartments that stores and displays products to customers for purchase. Generally, the sales floor of a typical retailer selling perishable products is a relatively uncontrolled and open environment where there are fluctuations in air flow, temperature, humidity, light exposure and moisture in any one area over time and between different areas of the sales floor. This is in contrast to more controlled environments involved in other portions of the supply chain, e.g., in distribution centers or delivery vehicles and refrigerated stock rooms. The retail sale floor is open to allow customers to move therethrough. Air flow from the outside environment can affect perishable products differently in different portions of the floor, such as those portions closer to open doorways and sky lights.

The display fixture 110 includes gas sensors 121, 122, and 123 for monitoring compartments 131, 132, and 133, respectively. A compartment may generally be described as a display area defined between dividers, such as a shelf, a bin, a rack, etc. In some embodiments, a gas sensor may gather gas emission from an unconfined area or space of a display fixture. While one gas sensor is shown in each of the compartments of the display fixture 110 in FIG. 1, each compartment may include a set of any number of sensors. The sensors may also be located in different areas of the compartment. The gas sensors 121, 122, and 123 may be configured to measure any gas released by the perishable item during ripening and/or decay. For example, the gas sensors 121, 122, and 123 may measure one or more of ethylene, ammonia, acetylene, nitrogen, carbon dioxide, oxygen. In some embodiments, the sensors may be selected based on the type of perishable item they are intended to measure. In some embodiments, the display FIG. 110 may be equipped with other sensors such as temperature moisture, and weight sensors to supplement the data collected by the gas sensors 121, 122, and 123. In some embodiments, the display fixture may further include a microprocessor and/or a communication module for communicating the data gathered by the sensor to the gas emission monitor 150. The communication may be via one or more of WiFi, long or short range radio frequency communication channel, wired connection, local area network, the Internet, and the like.

Each compartment of the display fixture 110 may contain a different type of product. For example, in FIG. 1, compartment 131 contains apples, compartment 132 contains pineapples, and compartment 133 contains carrots. The sensor(s) 121, 122, and 123 associated with each of the compartments 131, 132, and 133 are configured to collect gas emission measurement data from the items in the compartment. For example, gas sensor 121 is configured to read the collective gas emission of any and all apples in compartment 131. While fruits are shown in FIG. 1, the compartments 131, 132, and 133 may be used to hold any type of perishable item such as produce, dairy, meat, seafood, plant, floral, bakery goods, deli and prepared meals etc. Generally, the gas sensors may be used to monitor any perishable food or non-food item that releases gas without departing from the spirit of the present disclosure.

The gas emission monitor 150 receives the gas emission measurement from the gas sensors 121, 122, and 123. The gas emission monitor 150 may be one or more a computing device attached to the display fixture 110, a local computing device located in the same premise as the display fixture 110, or a remote computing device. The gas emission monitor 150 may be generally described as a control circuit and may be any processor based computing device such as a personal computer (PC), a portable device, a server, a cloud computing device, etc. In some embodiments, the functionalities of the gas emission monitor 150 described herein may be performed by two or more separately implemented computing devices. The gas emission monitor 150 may include a processor 152 and a memory 154.

The processor 152 may be configured to compare the gas emission measurements from the gas sensors 121, 122, and 123 with gas emission data from stored in a gas emission database 160. The comparison is described in more detail below with reference to FIGS. 2-4 below. The gas emission monitor 150 may further include or be accessible by user interface devices for a user to interact with the collected gas emission data.

The memory 154 may store a set of instructions executable by the processor to process the data collected from the gas sensors 121 as described with reference to FIGS. 2-4. The memory 154 may further store a history of gas sensor readings. For example, the gas sensor 122 may be configured to take a gas measurement every 10 minutes, and the memory 154 may store a log of such readings. The memory 154 may further store other data used in analyzing the gas emission data such as a store's planogram, a store's inventory information, product throughput data, projected sales data, product usage information etc. Planograms generally refers to a schematic or a floor plan that defines where and when products should be placed on each shelving unit of a retail space.

The gas emission database 160 may store a plurality of gas emission profiles, each profile being associates with one or more of a genus, a species, a variety, a cultivar, a growth location, and a growth time of a perishable product. For example, a profile may be associated with Gala apples, and a separate profile may be associated with Fuji apples. In another example, different profiles may be associated with Gala apples grown in California Central Valley and in Northern New Zealand. In yet another example, Chandler strawberries grown organically in southern California may have a different profile from Chandler strawberries grown conventionally in the same region. Each gas emission profile may be based on studies of the particular product category's typical gas emission during ripening and decay. In some embodiments, a gas emission profile may be a chart of the typical amount of ethylene released by a perishable product as it ripens and/or decays. In some embodiments, a profile may include emission data of two or more gasses. Each profile may be uniquely associated with a category and may be made based on studies and experiments performed on other items of the same category. For example, a profile for Gala apples may be generated by measuring the gas emission of one or more groups of Gala apples shortly after harvest until expiration under a controlled environment or in a retail environment. In some embodiments, data collected by the gas sensors 121, 122, and 123 in a retail environment are added to the data in the gas emission database to generate and/or supplement gas emission profiles for later use. The gas emission database 160 may be integrated, separately implemented, local, and/or remote from the memory 154 of the gas emission monitor 150.

By comparing the gas emission reading from the display fixture 110 and the stored gas profile, the processor 152 may estimate the freshness and/or the remaining shelf life of the perishable item. For example, the processor 152 may estimate a best-by date and/or an expiration date for the item. In some embodiments, the profile may indicate a mixture of gasses that can be used to identify the perishable product. For example, gas sensors 121, 122, and 123 may detect a mixture of two or more gasses in a compartment and the processor is able to determine what type of item is in the compartment based on the presence and/or constitution of the one or more detected gases.

While only one display fixture 110 and one gas emission monitor 150 is shown in FIG. 1, a monitoring system may include any number of display fixtures and gas emission monitors sharing sensor measurements and/or stored gas emission data.

In some embodiments, the sensors would communicate the type of product that is displayed on the fixture, the length of time that the product had been on the fixture, and the expected life span remaining on the product on the fixture. This information may be sent to store or cloud based servers, from which specific actions could be determined. Examples of the types of decisions that include: identifying product that has been received in the store, but has not been put on the sales floor, identifying product that is nearing spoilage and should be marked down to facilitate rapid sale, identifying product that should have been sold through to make space for arriving new products that are intended to be placed where the existing products are remaining and identifying compliance of fixture product with assigned floor plan. The system could be implemented with fresh display fixtures that include sensors and WiFi, Bluetooth, NFC, or wired communication enabled computing devices. Existing fixtures may also be retrofitted to include gas emissions sensors.

Figure 2:
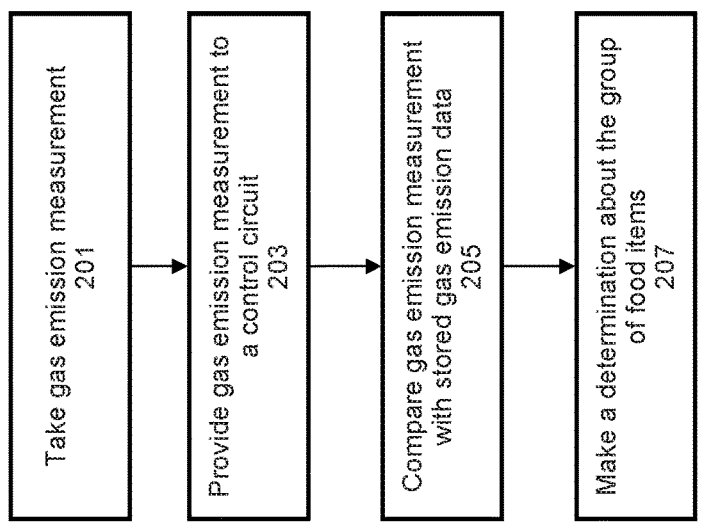
FIG. 2 is a flow diagram of a method in accordance with several embodiments.

Referring now to FIG. 2, a method of monitoring merchandise in a retail environment is shown. The method shown in FIG. 2 may be performed by the system shown in FIG. 1 or any system including one or more control circuits, such as computing devices, processor-based devices, and the like.

In step 201, gas emission is taken at a display fixture with one or more gas sensors. The gas sensors may be attached to a display fixture or be integrated into the structure of the display fixture that is configured to stores and displays for sale a group of perishable items. The gas sensors are configured to measure the gas emission of any item within an area, such as a compartment, section or shelf, of the display fixture. For example, the gas emission measurement may be of all the apples in a bin, all the cabbage between two dividers, etc. In some embodiments, two or more different gasses are measured by sensors in step 201. In some embodiments, step 201 is repeated periodically to provide history of the perishable item's gas emission to a control circuitry.

In step 203, the gas emission measurement taken in step 201 is provided to a control circuitry. The control circuit may be one or more of a computing device attached to or near the display fixture, a computing device in the same retail establishment as the display fixture, or a remote computing device. For example, the sensor data may be provided to a cloud-based server or a local computer for analysis. The gas emission measurement may be communicated to the gas emission monitor via a wired or wireless connection.

In step 205, the control circuit compares the measured gas emission with stored gas emission data. In some embodiments, a category associated with the measured perishable items is first determined. For example, the control circuit may match the gas emission measurement with one of a plurality of possible categories based on the type and the constitution of the gas(es) detected. In addition to data related to the gas(es) collected directly from the sensors, data regarding the past, present and future product included for the display unit, as well as current inventory information within the store may be utilized as a means to determine the type of product that the sensors detect. In some embodiments, the category may be determined based on the location of the sensor and a store planogram. For example, the location of the sensor may be matched with the designated location of an item. In some embodiments, the category of the item may be provided by other sensors such as a radio frequency identification (RFID) reader or a barcode scanner. The category of the group of perishable items may correspond to one or more of a genus, a species, a variety, a cultivar, a growth location, and a growth time of the item. The comparison may be based on comparing a history of the item's current gas emission with an emission over time profile of the matching category. For example, the control circuit may determine which point of the emission curve of the profile best matches the measured item's current condition based on the type and/or concentration of the detected gas. In some embodiments, the stored gas emission data may be one or more threshold values. For example, the stored gas emissions data may be one or more values of ethylene concentration corresponding to one or more stages of the item's ripening and/or decay. The threshold values may correspond to different actions to be taken, for example, there may be threshold values for level one discount, level two discount, and discard. In some embodiments, a history of gas emission reading is compared to the stored emission profile. For example, the rate of change in the measured gas emission over time (for example, last 3 hours, last day) may be compared to the rate of change in a stored profile to determine the freshness of the product.

In step 207, the control circuit makes a determination about the group of perishable items. The determination may be one or more of: estimated freshness, estimated expiration date, item presence, item location, and item type. In some embodiments, the determination may be whether the correct item is present in the correct location. For example, based on shipment delivery information, the control circuit may expect strawberries to be in a compartment associated with a sensor and determine whether strawberries are indeed present based on whether the measurements taken by the gas sensor matches known range of gas emission of strawberries. In some embodiments, control circuit may determine the remaining lifespan of the item. The gas measurement may be compared to stored gas emission data to determine an estimated expiration date of the item. For example, as described in step 205, the concentration of one or more measured gases may be compared with stored gas emission data to determine which stage of ripening and/or decay best match the measured item. The expiration date generally refers to the best-by date and/or the date that the food item becomes undesirable or unsafe for use or consumption.

In some embodiments, the control circuit furthers determines whether to apply a discount to the group of perishable items based on the determination. For example, if the item is about to expire, the store may apply a discount to the item to try to increase the sales rate of the item. In some embodiments, the determination may further take into account a forecasted rate of sales, an expected time between purchase and use by a customer, and incoming inventory information. For example, if an item still has 10 days until expiration but is not expected to be used by users until 7 days after purchase, the system may price the item to sell through within 3 days. In some embodiments, if the item still has 10 days of lifespan until expiration but another product that will occupy the same space is scheduled to arrive in 5 days, the system my price the item to sell through within 5 days. In some embodiments, different levels of discount may be applied based on the estimated proximity of the expiration date.

Figure 3:
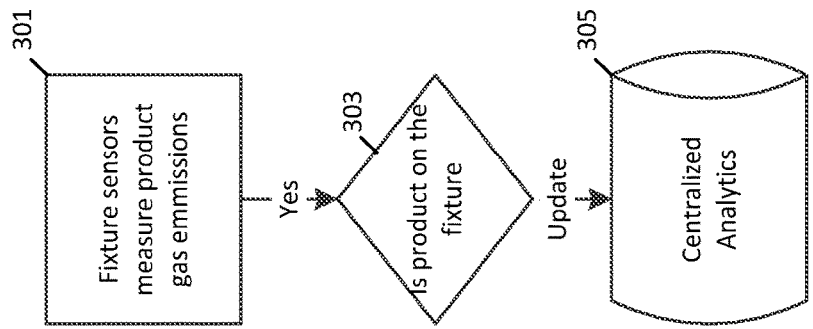
FIG. 3 is a flow diagram of a general process in accordance with several embodiments.

Now referring to FIG. 3, a process for determining whether a product is on the fixture is shown. In step 301, fixture sensor measure product gas emission. The fixture sensor may be configured to measure gas emission of items in an area of the fixture. In some embodiments, step 301 may be similar to step 201 of FIG. 2. In step 303, the system determines whether the product is on the fixture. Product may generally refer to any perishable merchandise in a retail environment such as produce, meat, and diary. Fixture may generally refer to any storage and display fixtures on the retail floor, such a table, a shelf, a rack, a refrigerator and the like. In some embodiment, the system determines whether any product is on the fixture. In some embodiments, the system determines whether the detected gas emission matches what is supposed be on the fixture. In some embodiments, the system is configured to identify the product based on the gas emission measure. After step 303, the determined information from step 303 is sent to a centralized analytics database 305 for storage and further utilization. For example, the data in the centralized analytics database 305 may be used to determine whether the store's planogram is being followed. The data may also be used to verify the product throughput and/or determine whether discount should be applied to one or more products. Centralized data may also be used to provide chain wide visibility to product decomposition rates, allowing for enhanced supply chain planning from agricultural production to retail sale.

Figure 4:
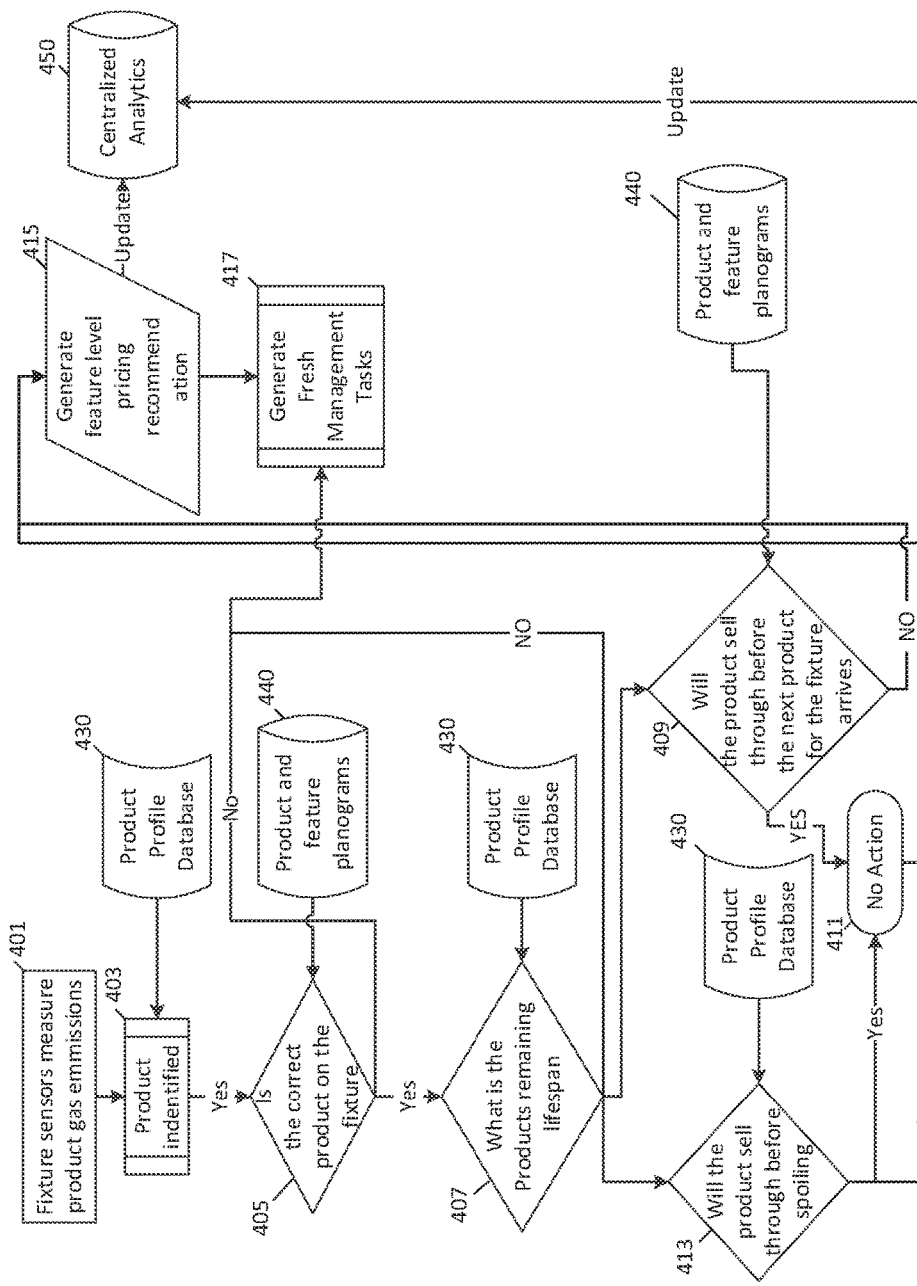
FIG. 4 is a flow diagram of a process in accordance with several embodiments.

Now referring to FIG. 4, a process for monitoring perishable products is shown. The method shown in FIG. 4 may be performed by the system shown in FIG. 1 or any system including one or more control circuitry, computing device, processor-based device, and the like.

In step 401, fixture sensors measure product gas emission of any product in a space of the display fixture associated with the sensor. In step 403, the product is identified. The identification of the product may be based on information stored in a product profile database 430. For example, the measured gas emission may be compared to several gas emission profiles to find a match. When the product is identified, in step 405, the system determines whether the correct product is on the fixture. Step 405 may be based on information in the product and feature planograms database 440. For example, the system may determine whether the identified product matches the intended product at the location of the sensor based on the planograms of the store. If the product on the fixture does not match the planogram, the process may move to step 417 to generate a fresh management task. For example, a task may be that a store clerk should remove the incorrect product and/or place the correct product on the fixture.

In step 407, the system determines the product's remaining lifespan. The determination may be based on comparing the sensor measurements with stored gas emission data in the product profile database 430. The system may compare the current gas emission and match it to a data point in a stored gas emission profile to determine the remaining lifespan. In step 413, the system determines whether the product will sell through before spoiling. If the product will sell through, no action is taken in step 411. If the product is not expected to sell through by the expiration date, the process moves to step 415 and a feature level pricing recommendation is generated. The pricing recommendation would be applied to the entire group of products, for example, all Gala apples on the sales floor. The pricing recommendation is set at a level such that the estimated sell through date would be before the spoiling date. In some embodiments, the targeted sell through date may be modified based on usage habit information. For example, if customers typically do not cook a potato until at least five days after purchase, the targeted sell through date may be set at 5 or more days before the estimate spoilage date. The pricing recommendation may be set according to such adjustment.

After step 407, the system may also determine whether the product will sell through before the next product for the fixture arrives in step 409. Step 409 may be based on information in the product and feature planograms database 440. For example, the arrival of the next product for the fixture may be provided in the inventory and shipment information stored in the product and feature planograms database 440. If the product is expected to sell through prior to the arrival of the next product, no action is taken in step 411. If the product is not expected to sell through prior to the arrival of the next product, the process proceeds to step 415 and a feature level pricing recommendation is generated to increase the sales rate of the product to make space for the incoming product.

After a pricing recommendation is generated in step 415, a fresh management task is generated in step 417. The management task may include one or more of reviewing and approving the pricing recommendation, replacing signage, relocating product, generating an advertisement, and the like. In some embodiments, the fresh management task may be performed automatically by the system, manually by a retail worker, or by a combination of the two.

After a pricing recommendation is generated at 415 or no action is taken at step 411, the collected data and determinations are stored into a centralized analytics database 405. The information stored in the centralized analytics database 405 may be used to generate reports to help the retail store plan future planograms, set future prices, determine selection and orders for new products, forecast sales rates, and the like. In some embodiments, the centralized analytics information may be shared with farmer, producers, and shipper for the development of new products and procedures to improve the freshness of the products. In some embodiments, the data in the centralized analytics database 450 may also be used to update the information in the product profile database 430 and the product and feature planograms database 440 for further use.

The product profile database 430, the product and feature planograms database 440, and the centralized analytics database 450 may each be implemented in one or more physical devices and may be local or remote from the system described FIG. 1. One of more of these databases may be local to each retail location, shared among a geographical region, and/or shared among an entire organization or company.

Figure 5:
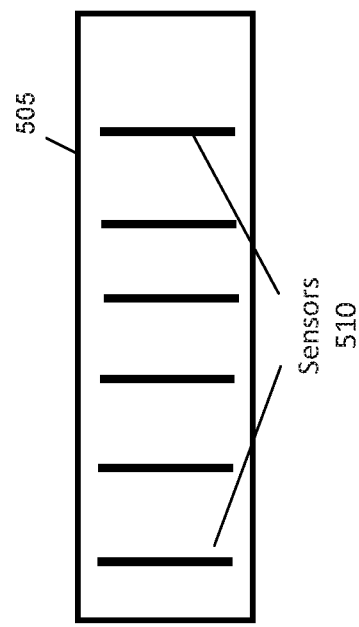

Now referring to FIG. 5, a display shelf 505 with a sensor array 510 is shown. The sensor array 510 may be placed at any portion of the fixture, including horizontal portion and/or the vertical portion of the display shelf 505. Each of the sensors in the sensor array 510 may be configured to measure the same type of gas(es) or different gasses. The sensors 510 may be attached and/or integrated into the structure of the display shelf 505. For example, the sensors may be imbedded into the shelf such that the surface of the shelf is even for storing and displaying the perishable products. Now referring to FIG. 6, a display table 605 with sensors 610 is shown. In FIG. 5, the sensors 610 are positioned diagonally in the four squadrons of the horizontal surface of a rectangular display table 605.

Figure 6:
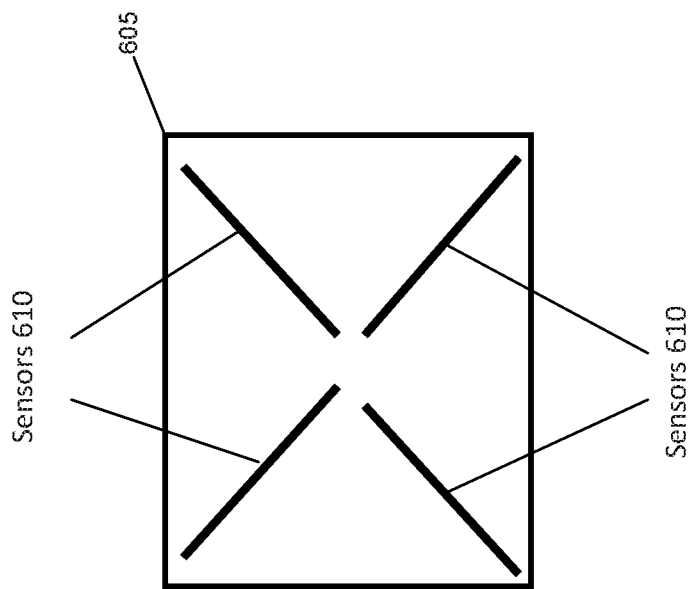
FIGS. 5-6 are illustrations of sensor layout on display units in accordance with several embodiments.

FIGS. 5 and 6 are provided as examples of possible sensor layout. Generally, gas sensors may be attached or integrated with display fixtures in any configuration that is able to measure gas emission from products stored and displayed on the fixture without departing from the spirit of the present disclosure.

In some embodiments, a system for automatically monitoring merchandise in a retail sales environment is provided. The system includes a display fixture configured to store and display for sale a group of perishable items and one or more gas emission sensors associated with the display fixture and configured to measure gas emissions from the group of perishable items. The system further includes a control circuit coupled to the one or more gas emission sensors and configured to receive a gas emission measurement taken at the display fixture, compare the gas emission measurement with stored gas emission data associated with a category of the group of perishable items; and make a determination corresponding to the group of perishable items based on the comparison.

In some embodiments, a method for automatically monitoring merchandise in a retail sales environment is provided. The method includes taking, at a display fixture, a gas emission measurement with one or more gas emission sensors associated with the display fixture, the display fixture configured to store and display for sale the group of perishable items, providing the gas emission measurement to a control circuit, comparing, by the control circuit, the gas emission measurement with stored gas emission data associated with a category of the group of perishable items, and making, by the control circuit, a determination corresponding to the group of perishable items based on the comparing.

In some embodiments, an apparatus for automatically monitoring merchandise in a retail sales environment is provided. The apparatus includes a control circuit, and a non-transitory computer readable memory storing a set of instructions executable by the control circuit. The instructions executable by the control circuit being configured to cause the control circuit to perform the steps of: receive a gas emission measurement measured with one or more gas emission sensors associated with a display fixture configured to store and display for sale a group of perishable items, compare the gas emission measurement with stored gas emission data associated with a category of the group of items; and make a determination corresponding to the group of items based on the comparison.

In some embodiments, a method of automatically monitoring merchandise in a retail sales environment is provided. The method includes a control circuit receiving a gas emission measurement measured with one or more gas emission sensors associated with a display fixture configured to store and display for sale a group of perishable items, comparing the gas emission measurement with stored gas emission data associated with a category of the group of items, making a determination corresponding to the group of items based on the comparing.

Those skilled in the art will recognize that a wide variety of other modifications, alterations, and combinations can also be made with respect to the above described embodiments without departing from the scope of the invention, and that such modifications, alterations, and combinations are to be viewed as being within the ambit of the inventive concept.

What is claimed is:

1. A system for automatically monitoring gas emissions of perishable goods in a retail sales environment comprising:
   a display fixture configured to store and display for sale a group of perishable items;
   one or more gas emission sensors integrated into a structure of the display fixture and configured to measure gas emissions from the group of perishable items on the display fixture;
   a control circuit coupled to the one or more gas emission sensors and configured to:
      receive a gas emission measurement taken at the display fixture;
      add the gas emission measurement to a history of gas emission measurements associated with the group of perishable items;
      compare the history of gas emission measurements of the group of perishable items with stored gas emission data associated with a category of the group of perishable items, wherein the stored gas emission data comprises a gas emission over time profile associated with the category;
      make a determination corresponding to the group of perishable items based on the comparison; and
      determine whether to apply a discount to the group of perishable items based on the determination and one or more of a forecasted rate of sales, an expected time between purchase and use by a customer, and incoming inventory information.

2. The system of claim 1, wherein the group of perishable items comprises one or more of produce, dairy, meat, seafood, plant, floral, deli, prepared meals and bakery goods.

3. The system of claim 1, wherein the category of the group of perishable items corresponds to one or more of a genus, a species, a variety, a cultivar, a growth location, and a growth time.

4. The system of claim 1, wherein the control circuit is further configured to:
   identify the group of perishable items based on the gas emission measurement and determine the category for the group of perishable items.

5. The system of claim 1, wherein the determination comprises a determination of one or more of: freshness, estimated expiration date, item presence, item location, and item type.

6. The system of claim 1, wherein the control circuit is further configured to:
   collect gas emission measurements from a plurality of groups of perishable items and compare the collected gas emission measurements with a planogram of a retail space to determine whether the planogram is followed.

7. A method for automatically monitoring gas emissions of perishable goods in a retail sales environment comprising:
   taking, at a display fixture, a gas emission measurement with one or more gas emission sensors integrated into a structure of the display fixture, the display fixture being configured to store and display for sale a group of perishable items on the display fixture;
   providing the gas emission measurement to a control circuit;
   adding the gas emission measurement to a history of gas emission measurements associated with the group of perishable items;
   comparing, by the control circuit, the history of gas emission measurements of the group of perishable items with stored gas emission data associated with a category of the group of perishable items, wherein the stored gas emission data comprises a gas emission over time profile associated with the category;

making, by the control circuit, a determination corresponding to the group of perishable items based on the comparing; and determining whether to apply a discount to the group of perishable items based on the determination and one or more of a forecasted rate of sales, an expected time between purchase and use by a customer, and incoming inventory information.

8. The method of claim 7, wherein the group of perishable items comprises one or more of produce, dairy, meat, seafood, plant, floral, deli, prepared meals and bakery goods.

9. The method of claim 7, wherein the category of the group of perishable items corresponds to one or more of a genus, a species, a variety, a cultivar, a growth location, and a growth time.

10. The method of claim 7, further comprising:
identifying the group of perishable items based on the gas emission measurement and determining the category for the group of perishable items.

11. The method of claim 7, wherein the making the determination step comprises making a determination of one or more of: freshness, estimated expiration date, item presence, item location, and item type.

12. The method of claim 7, further comprising:
collecting gas emission measurements from a plurality of groups of perishable items and comparing the collected gas emission measurements with a planogram of a retail space to determine whether the planogram is followed.

13. An apparatus for automatically monitoring gas emissions of perishable goods in a retail sales environment comprising:
a control circuit; and
a non-transitory computer readable memory storing a set of instructions executable by the control circuit and configured to cause the control circuit to perform the steps of:
receive a gas emission measurement measured with one or more gas emission sensors integrated into a structure of a display fixture configured to store and display for sale a group of perishable items on the display fixture;
add the gas emission measurement to a history of the gas emission measurements associated with the group of perishable items;
compare the history of gas emission measurements of the group of perishable items with stored gas emission data associated with a category of the group of perishable items;
make a determination corresponding to the group of perishable items based on the comparison; and
determine whether to apply a discount to the group of perishable items based on the determination and one or more of a forecasted rate of sales, an expected time between purchase and use by a customer, and incoming inventory information.

14. A method of automatically monitoring gas emissions of perishable goods in a retail sales environment comprising:
by a control circuit,
receiving a gas emission measurement measured with one or more gas emission sensors integrated into a structure of a display fixture configured to store and display for sale a group of perishable items on the display fixture;
adding the gas emission measurement to a history of the gas emission measurements associated with the group of perishable items;
comparing the history of gas emission measurements of the group of perishable items with stored gas emission data associated with a category of the group of perishable items, wherein the stored gas emission data comprises a gas emission over time profile associated with the category;
making a determination corresponding to the group of perishable items based on the comparing; and
determining whether to apply a discount to the group of perishable items based on the determination and one or more of a forecasted rate of sales, an expected time between purchase and use by a customer, and incoming inventory information.

* * * * *